United States Patent [19]

Buisman

[11] Patent Number: 5,354,545
[45] Date of Patent: Oct. 11, 1994

[54] PROCESS FOR THE REMOVAL OF SULPHUR COMPOUNDS FROM GASES

[75] Inventor: Cees J. N. Buisman, Harich, Netherlands

[73] Assignee: Paques B.V., Harich, Netherlands

[21] Appl. No.: 70,336

[22] PCT Filed: Dec. 4, 1991

[86] PCT No.: PCT/NL91/00250

§ 371 Date: May 26, 1993

§ 102(e) Date: May 26, 1993

[87] PCT Pub. No.: WO92/10270

PCT Pub. Date: Jun. 25, 1992

[30] Foreign Application Priority Data

Dec. 4, 1990 [NL] Netherlands .................. 9002661

[51] Int. Cl.[5] ................................. C01B 17/00
[52] U.S. Cl. .................. 423/242.1; 423/232; 423/243.01; 423/576.2; 423/576.4; 423/DIG. 17; 210/601
[58] Field of Search .............. 423/221, 232, 242.1, 423/243.01, DIG. 17, 576.2, 514; 23/293 S; 425/576.4

[56] References Cited

U.S. PATENT DOCUMENTS

| 2,138,214 | 7/1935 | Shiffler ........................ 423/576.4 |
| 3,839,549 | 10/1974 | Deschamps et al. ............ 423/514 |
| 4,242,448 | 12/1980 | Brown, III ...................... 435/42 |
| 4,579,727 | 4/1986 | Cronkright et al. ............ 423/573 R |

FOREIGN PATENT DOCUMENTS

| 81347 | 5/1895 | Fed. Rep. of Germany ...... 423/514 |
| 2305630 | 9/1973 | Fed. Rep. of Germany ... 423/576.4 |
| 2831209 | 2/1979 | Fed. Rep. of Germany ...... 423/514 |
| 2328501 | 5/1977 | France . |
| 5348094 | 5/1978 | Japan .............................. 423/232 |
| 25204 | 11/1914 | Netherlands .................... 423/514 |
| 8801009 | 11/1989 | Netherlands . |
| 711142 | 1/1980 | U.S.S.R. ........................ 423/576.2 |

*Primary Examiner*—Gary P. Straub
*Assistant Examiner*—Timothy C. Vanoy
*Attorney, Agent, or Firm*—Young & Thompson

[57] ABSTRACT

A process for the removal of sulphur compounds from a gaseous effluent, comprising the steps of: a) contacting the gaseous effluent with an aqueous solution wherein sulphur compounds are dissolved; b) adjusting the concentration of buffering compounds such as carbonate and/or bicarbonate and/or phosphate in the aqueous solution to a value between 20 and 2000 meq/l; c) subjecting the aqueous solution containing sulphide to sulphide-oxidizing bacteria in the presence of oxygen in a reactor wherein sulphide is oxidized to elemental sulphur; d) separating elemental sulphur from the aqueous solution; and e) recycling the aqueous solution to step a). This process is suitable for removing $H_2S$ from biogas, ventilation air etc. It can be used for removing $SO_2$ from combustion gases by introducing the additional step, after step a) and before step c), of subjecting the aqueous solution containing the sulphur compounds to a reduction of the sulphur compounds to sulphide. $H_2S$ and $SO_2$ removal is further enhanced by a residual sulphur content in the washing liquid of 1–50 g/l.

7 Claims, 1 Drawing Sheet

PROCESS FOR THE REMOVAL OF SULPHUR COMPOUNDS FROM GASES

The invention relates to a process for the removal of sulphur compounds from a gas flow, in particular from biogas, wherein the gas is washed with an aqueous washing liquid and the spent washing liquid is treated with oxygen and is subsequently reused as a washing liquid.

BACKGROUND OF THE INVENTION

The presence of sulphur compounds in gas flows is undesirable, because of their toxicity and their smell. Hydrogen sulphide ($H_2S$) is a harmful compound that is frequently present in gas flows, especially in biogas originating from anaerobic waste treatment. Sulphur dioxide is another noxious sulphur compound that is present in gas flows resulting from the combustion of fossil fuels. Other harmful sulphur compounds that may be present in gas flows include sulphur trioxide, carbon disulfide, lower alkyl mercaptans etc. Gaseous effluents containing these sulphur compounds must therefore be purified, before they can be discharged into the atmosphere.

A process for removal of $H_2S$ from a gas flow by scrubbing with a washing liquid and subsequently oxidising the absorbed sulphide is known from European patent application 229,587. According to that process, sulphide absorbed in the washing liquid is oxidized non-biologically, in the presence of a catalyst, to products including elemental sulphur which is separated from the system. However, loss of catalyst occurs in such a process, which is an environmental drawback and which increases costs. The known process is also relatively expensive because oxidation takes place using pressure.

A process frequently used is washing biogas with an aqueous liquid having an increased pH, typically a pH of about 11. This increased pH may be adjusted by the addition of sodium hydroxide or other alkalis. Such processes are known for example from European patent application 229,587. A drawback of scrubbers of this type is their high consumption of chemicals, resulting in relatively high operational costs. The price of sodium hydroxide has been increasing strongly recently as a result of a reduced production of chlorine. For many industries, savings in sodium hydroxide will therefore become important. Another disadvantage of this process is that it results in aqueous effluent contaminated with sulphide. According to NL-A-8801009 spent washing liquid from $H_2S$ removal from gases can be regenerated by subjecting it to sulphur-oxidizing bacteria in the presence of oxygen.

Another method consists in mixing the biogas with air or oxygen then conveying it into an oxidation reactor, wherein the sulphide is converted to sulphur, as is known from European patent application 224,889. A drawback of this method is that the reactor becomes rather expensive, because the mixture of biogas and oxygen is explosive, requiring safety precautions. The reactor should also be rather large because the conversion rate is strongly reduced by the low concentration of oxygen which is allowed in connection with the gas effluent requirements (explosion standards).

Known processes for the removal of sulphur dioxide from gaseous effluents involve washing the gas flow with an acidic aqueous washing liquid having a pH which is typically below 5.8. The dissolved $SO_2$ is usually oxidised and separated as calcium sulphate (gypsum).

SUMMARY OF THE INVENTION

The invention provides an integrated process for the removal of sulphur compounds, such as $H_2S$ and $SO_2$, from gaseous effluents, wherein chemical scrubbing and biological oxidation are combined. The process results in an effective purification without the need to continuously add alkali or other chemicals to the washing liquid or to add oxygen to the gas flow and without danger of explosion.

The process of the invention is characterized by carrying out the steps of:
 a) contacting the gaseous effluent with an aqueous solution wherein sulphur compounds are dissolved;
 b) adjusting the concentration of buffering compounds such as carbonate and/or bicarbonate and/or phosphate in the aqueous solution to a value between 20 and 2000 meq/l;
 c) subjecting the aqueous solution containing sulphide to sulphide-oxidizing bacteria in the presence of oxygen in a reactor wherein sulphide is oxidized to elemental sulphur and hydroxide;
 d) separating elemental sulphur form the aqueous solution; and
 e) recycling the aqueous solution to step a).

When the gaseous effluent contains appreciable levels of oxidized sulphur compounds, in particular sulphur dioxide, the process comprises, after or before step b), the additional step of subjecting the aqueous solution containing the sulphur compounds to a reduction of the sulphur compounds to sulphide.

DESCRIPTION OF THE INVENTION

The first step of the process according to the invention consists in contacting the gaseous effluent with an aqueous washing liquid. This step can be perfomed in a gas scrubber which ensures an effective contact between the gas flow and the washing liquid.

An important feature of the present process is that the washing liquid is buffered, preferably at a pH between 6.0 and 9.0, depending on the nature of the gas flow to be treated and especially on the nature of the sulphur compounds to be removed. The buffering compounds must be tolerated by the bacteria present in the oxidation reactor. Preferred buffering compounds are carbonates, bicarbonates, phosphates and mixtures thereof, especially sodium carbonate and/or sodium bicarbonate. The concentration of the buffering compounds depends on the nature of the gas flow, and is generally adjusted to a value within the range of 20 to 2000 meg/l. When sodium carbonate is the buffering compound, its concentration is preferably adjusted to about 1 to 70 g/l. Where in this specification reference is made to bicarbonate and carbonate concentrations, these are expressed as the concentration by weight of $HCO_3^-$ and $CO_3^{--}$ ions respectively.

Addition of buffering compounds can be done after the washing liquid has left the gas scrubber, but also before it is fed into the scrubber. In case of carbonate/bicarbonate, the buffering compound can advantageously be added in the form of carbon dioxide, for example in the gas scrubbing step, when the gaseous effluent contains high levels of carbon dioxide.

Known autotrophic aerobic cultures, such as cultures of the genera Thiobacillus and Thiomicrospira, can be used as bacteria oxidizing sulphide to elemental sulphur (herein referred to as sulphide-oxidising bacteria) in the treatment of spent washing liquid in the presence of oxygen in step c).

The amount of oxygen fed into the washing liquid in the oxidation reactor is adjusted in such a way that the oxidation of the absorbed sulphide predominantly leads to the production of elemental sulphur. Such a process for the controlled oxidation of sulphur-containing waste water is described in Netherlands patent application 8801009.

The production of sulphur in the oxidation reactor will result in a sulphur slurry which is drawn off. The sulphur from this slurry is separated and processed by drying and optionally pruifying, and utilized.

It has been found to be advantageous when not all sulphur is drawn off, and thus the separation is carried preferably out discontinuously or partially, resulting in a washing liquid still containing sulphur. The sulphur concentration in the washing liquid is generally kept between 0.1 and 50 g/l, preferably between 1 and 50, and more preferably between 10 and 50 g/l (1–5% by weight). In particular, the sulphur separation rate is adjusted such that the washing liquid is recycled to the largest extent possible. The liquid recovered after processing of the separated sulphur can be returned to the washing liquid.

The advantages of the present process are:
1. there is hardly any need for chemicals (sodium hydroxide);
2. no catalyst is needed;
3. the required equipment is simple;
4. energy consumption is low;
5. no $CO_2$ is absorbed (after equilibrium has been established);
6. no waste effluent results, the sulphur may be sold.

Experiments have shown that the high (bi)carbonate concentrations do not negatively affect the bacterial activity.

REMOVAL OF HYDROGEN SULPHIDE

When $H_2S$ or other reduced volatile sulphur compounds such as lower alkyl mercaptans or carbon disulphide, have to be removed, e.g. from biogas, the spent washing liquid containing the sulphur compounds can be directly fed into the reactor containing the sulphide-oxidising bacteria. These reduced sulphur compounds, when dissolved, are referred to herein as "sulphide", but this term will be understood to include other reduced sulphur species such as dissolved hydrogen sulphide ($H_2S$ or $HS^-$), disulphide, polysulphides, thiocarbonates, alkanethiolates, etc.

The pH in the system is preferably kept at about 8–9, particularly at about 8.5. When the pH is lower, the $H_2S$ scrubbing efficiency is insufficient, whereas a higher pH inhibits the activity of most of the bacteria. At the start of the process according to the invention, an alkaline washing liquid will be used, or alkali will be added in the initial stage of the process. It was found surprisingly that, after an initial period, no alkali needs to be added any more, in particular when the gas flow also contains carbon dioxide such as in biogas.

The composition of the washing liquid is determined by:
1. the pH
2. the oxidation of sulphide As to the pH:

$CO_2$ which is present in the (bio)gas will also partially be absorbed in the washing liquid. As a result of the recycling of the washing liquid a carbon dioxide equilibrium will be established according to the following reactions:

$$H_2O + CO_2 \rightleftharpoons H_2CO_3 \rightleftharpoons HCO_3^- + H^+ \rightleftharpoons CO_3^{--} + 2H^+$$

The concentration of the dissolved carbonates produced depends of course on the $CO_2$ concentration in the gas to be purified. The carbonate concentration is about 4–70 g/l, when the $CO_2$ concentration in the gas is between 10 and 20%. The process is found to operate particularly effectively at such concentrations. A carbonate concentration of more than 70 g/l is not suitable, since it will adversely affect the activity of the bacteria in the oxidation reactor.

In a conventional scrubber absorbing $H_2S$ and $CO_2$ at high pH, the level of $CO_2$ absorption is much higher than in a scrubber as operated according to the present invention. The total amount of $CO_2$ absorbed depends on the $CO_2$ content of the gas flow, the pH of the scrubbing liquid and the gas flow conducted through the scrubber. In a conventionally operated scrubber the $CO_2$ saturation value (i.e. the $HCO_3^-$ and $CO_3^{--}$ concentration) is not reached, because of the high pH and the short contact time between gas and washing liquid. In the present process however, the carbonate and bicarbonate concentrations of the washing liquid will be equal to or close to the saturation level, because of the relatively low pH (and thus the relatively low saturation value, which is about 3–5 g/l for $HCO_3^-$ and about 0.1–0.3 g/l for $CO_3^{--}$ at pH 8.5) and low gas/liquid flow ratio, and because the system is cyclic.

After an equilibrium has thus been established, the washing liquid will no longer absorb $CO_2$ and no more or very little alkali will be needed for neutralizing the $CO_2$. The $CO_2$ which is stripped in the oxidation step can be replenished in the absorption step.

When the $CO_2$ content in the gas is lower, $CO_2$ or (bi)carbonate may be added, preferably to a level of 100–1500, more preferably 200–1200, and most preferably between 400 and 1200 meq/l.

As to sulphide oxidation:

As a result of the oxidation of sulphide with oxygen the concentration of sulphide in the washing liquid will not increase. The sulphur content in the liquid will increase instead, according to the following reactions, which illustrate why the pH of the washing liquid does not decrease.

$$2H_2S + O_2 \rightarrow 2S + 2H_2O$$

or:

$$(nS \rightarrow S_n)$$

$$2HS + O_2 \rightarrow 2S \rightarrow 2OH^-$$

The sulphide concentration in the spent washing liquid having a pH of about 8.5 will normally be about 80–100 mg/l, expressed as sulphur. This is a lower concentration than the concentration that is obtained in a conventional $H_2S$ scrubber operating at a pH of 10 to 11. Therefore, the scrubber will have to be larger than a conventional scrubber and a higher water/gas flow ratio will be used, for example a water flow to gas flow ratio of 0.1 to 0.2.

It was found that a sulphur concentration of 0.1–50 g/l, in particular 1–50 g/l in the washing liquid improves the removal of H2S from the biogas, while at the same time an effective sulphur separation is ensured. The improved H2S removal results from polysulphide production according to the reaction: $HS^- + S_n \rightarrow HS_{(n+1)}^-$ which causes the absorption equilibrium to shift towards increased absorption. At a sulphide concentration of 90 mg/l in the spent washing liquid, at least half of the sulphide will be bound as polysulphide.

The present process has the advantage that neutralizing agents are not necessary to lower the pH after the scrubber, and therefore no salts are built up in the recirculating washing liquid.

REMOVAL OF SULPHUR DIOXIDE

When the gaseous effluent contains appreciable levels of sulphur compounds having higher oxidation states, particularly sulphur dioxide, but also sulphur trioxide or other oxidised sulphur compounds, an additional process step is required to reduce the sulphur compounds to sulphide.

These sulphur compounds having higher oxidation states, when dissolved, are referred to herein as "sulphite", but this term will be understood to include other oxidised species such as dissolved sulphur dioxide, hydrogen sulphite (bisulphite), sulphate, thiosulphate, etc.

Reduction of sulphite to sulphide can be performed by chemical means, but preferably a biological reduction is carried out using an anaerobic reactor. Suitable bacteria for use in the anaerobic reactor to reduce sulphite to sulphide include bacteria reducing sulphur compounds (herein referred to as sulphur-reducing bacteria) such as species of the genera Desulfovibrio, Desulfotomaculum, Desulfomonas, Desulfobulbus, Desulfobacter, Desulfococcus, Desulfonema, Desulfosarcina, Desulfobacterium and Desulformas. In general, these bacteria are available from various anaerobic cultures and/or grow spontaneously in the anaerobic reactors.

The pH of the washing liquid is preferably maintained at a level of about 6 to 7. This is higher than in conventional SO2 scrubbers in processes wherein the sulphur dioxide is fixed as gypsum, which typically use a pH below 5.8. This increased pH results in a more efficient SO2 scrubbing. The pH may be adjusted by the addition of buffering agents. Preferably, carbonate or bicarbonate is added to a level of 20–100 meq/l, for example about 30 meq/l.

The washing liquid may be conducted through the scrubber several times before being regenerated. In such a process, the (bi)carbonate concentration of the washing liquid is preferably higher, e.g. 50–200 meq/l.

When SO2 is removed from gaseous effluents, the presence of sulphur in the washing liquid was also found to be advantageous. Reaction of sulphur with SO2 (or with HSO3−) results in thiosulphate formation. In the absence of sulphur, SO2 may be further oxidized to sulphate by the oxygen which is often present in combustion gases as well. As sulphate requires more reduction equivalents (electron donor) than thiosulphate does, less electron donor (such as alcohol) is required in the reduction reactor as a result of the presence of sulphur in the washing liquid. In addition, the absorption capacity of the washing liquid is increased by the conversion to thiosulphate. The sulphur level is between 0.1 and 50 g/l, preferably between 1 and 50, and most preferably between 10 and 50 g/l.

DESCRIPTION OF THE FIGURES

The process for removing H2S and other reduced sulphur compounds such as lower alkyl mercaptans is illustrated with reference to FIG. 1. Biogas contaminated with H2S (1) enters the scrubber (2) at the bottom and is treated with washing liquid (9). Purified gas (3) leaves the reactor at the top. The washing liquid (10) which is now contaminated with sulphide leaves the reactor at the bottom and is fed into the oxidation reactor (5), where sulphide is converted to sulphur by the bacteria present therein and oxygen. The reactor is supplied with oxygen by an aeration device (4). Spent air (6) will have to be treated in a compost filter (7) because of its stench. The treated air (8) can be discharged without problems. The production of sulphur will result in a sulphur slurry (11) which is partially drawn off. The sulphur (12) from this slurry can be dried and utilised. The separated aqueous solution (13) is recycled as much as possible in order to save nutrients and alkalinity. If necessary, alkali may be added to flow (9).

The process for removing SO2 and other oxidised sulphur compounds is illustrated with reference to FIG. 2.

Figure 1:
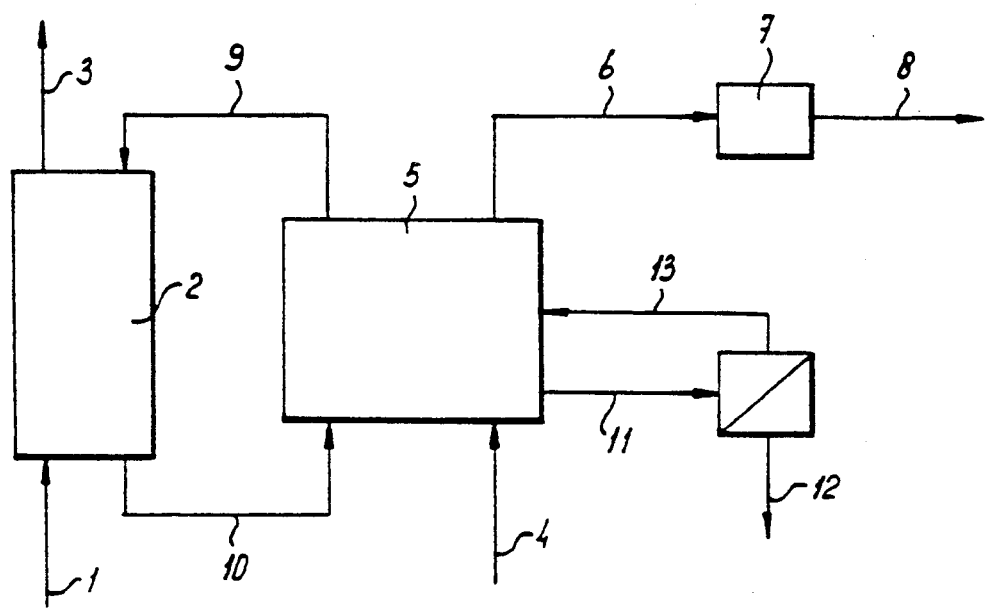
Figure 2:
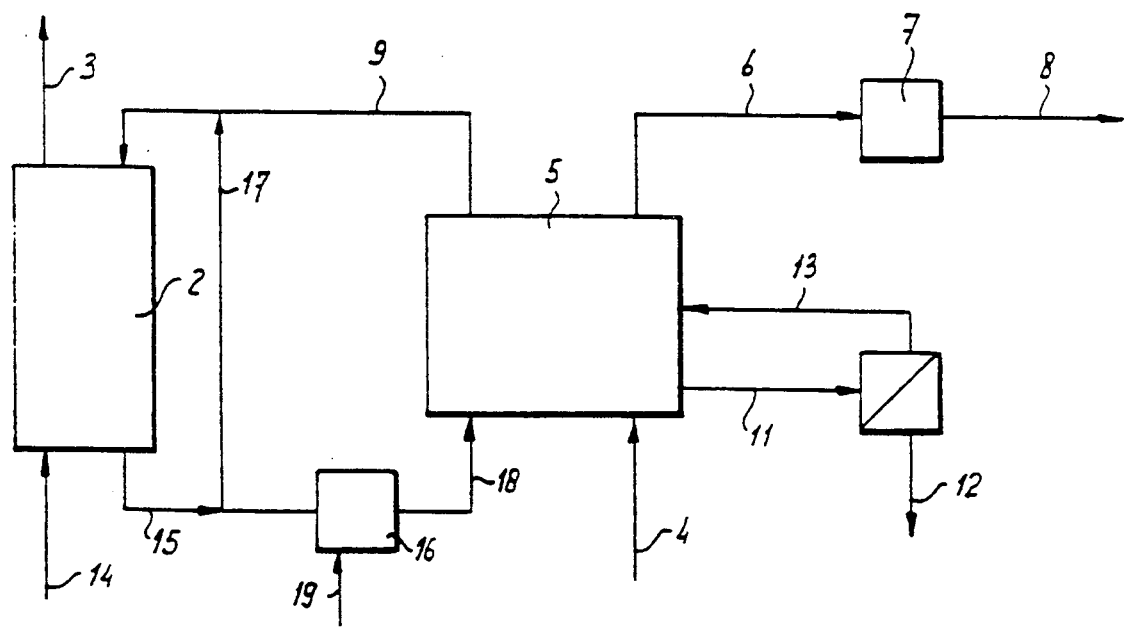

The combustion gas containing SO2 (14) enters the scrubber (2) in a similar way. The washing liquid (15) containing sulphite is fed into the reduction reactor (16) wherein sulphite is converted to sulphide by anaerobic bacteria. A part of the spent washing liquid may be directly returned to the washing liquid (9) by a shortcut (17). The reduced washing liquid (18) is then treated in the oxidation reactor (5) as in the process of FIG. 1. An electron donor, e.g. alcohol, is added through (19). Fresh carbonate solution may be added through (19) or elsewhere in the cycle.

Any gaseous effluent that can be treated with an alkali scrubber can also be purified with the process described herein, provided that the temperature is not too high for the biological activity. The process according to the invention is therefore not restricted to biogas. It can also be used for treating combustion gases and ventilation air; in the latter case a phosphate buffer having a concentration of about 50 g/l is preferred.

EXAMPLE

An operating example for H2s removal is presented in Table A; numbers in the table correspond with the numbers in the accompanying FIG. 1.

The oxidation reactor (5) is a "fixed-film" reactor or a "trickling filter" and contains about 6 m³ of carrier material having a surface area of 200 m²/m³. The dimensions of the scrubber (2) are (diameter × height) 0.5 × 2.5 m. The reactor is filled with Bionet 200 rings (NSW company).

TABLE A

| flow | | |
|---|---|---|
| 1 | concentration H2S | 0.8–1.0% |
| 1 | concentration CH4 | 79% |
| 1 | concentration CO2 | 20% |
| 1 | flow rate | 200 m³/h |
| 3 | concentration H2S | 150 ppm |
| 3 | concentration CH4 | 79% |
| 3 | concentration CO2 | 20% |
| 10 | flow rate | 200 m³/h |
| 10 | sulphide concentration | 89 mg/l |

TABLE A-continued

| flow | | |
|---|---|---|
| 10 | bicarbonate concentration | 7 g/l |
| 10 | sulphur concentration | 3% |
| 10 | pH | 8.2 |
| 10 | flow rate | 30 m$^3$/h |
| 9 | sulphide concentration | <5 mg/l |
| 9 | sulphur concentration | ca 3% |
| 9 | pH | 8.4 |
| 9 | flow rate | 30 m$^3$/h |

I claim:

1. Process for the removal of sulphur compounds selected from hydrogen sulfide, alkyl mercaptans and carbon disulfide from a gaseous effluent, comprising the steps of:
   a) contacting the gaseous effluent with an aqueous solution wherein sulphur compounds are dissolved;
   b) adjusting the concentration of buffering compounds selected from carbonate, bicarbonate and phosphate in the aqueous solution to a value between 20 and 2000 meq/l and maintaining the pH of the aqueous solution to between 6 and 9 throughout the process;
   c) subjecting the aqueous solution containing sulphides to sulphide-oxidizing bacteria in the presence of oxygen in a reactor wherein sulphide is oxidized to elemental sulphur;
   d) separating elemental sulphur from the aqueous solution, so that the aqueous solution contains 0.1-50 g of elemental sulphur per l; and
   d) recycling the aqueous solution to step a).

2. Process of claim 1, wherein the concentration of buffering compounds in step b) is adjusted to a value between 100 and 1500 meq/l.

3. Process of claim 2, wherein in step b) the buffering compounds comprise carbonate and/or bicarbonate the concentration of which is adjusted to a value between 200 and 1200 meq/l.

4. Process according to claim 1, wherein the pH of the aqueous solution is adjusted to between 8 and 9.

5. Process according to claim 1, wherein in step a) the gaseous effluent contains carbon dioxide.

6. Process according to claim 1, wherein after step d) the aqueous solution contains 1-50 g of elemental sulphur per l.

7. Process according to claim 6, wherein in step e) the aqueous solution contains 10-50 g of elemental sulphur per l.

* * * * *